United States Patent
Diez Garcia et al.

(10) Patent No.: US 10,274,445 B2
(45) Date of Patent: Apr. 30, 2019

(54) METHOD FOR MEASURING THE PRESENCE OF WATER IN GAS OIL FILTERS AND WATER SENSOR FOR CARRYING OUT SAID METHOD

(71) Applicant: CEBI ELECTROMECHANICAL COMPONENTS SPAIN, S.A., Villatuerta (Navarra) (ES)

(72) Inventors: Sergio Diez Garcia, Villatuerta (ES); Jose Luis Landatxe Zugarramurdi, Villatuerta (ES)

(73) Assignee: CEBI ELECTROMECHANICAL COMPONENTS SPAIN, S.A., Villatuerta (Navarra) (ES)

( * ) Notice: Subject to any disclaimer, the term of this patent is extended or adjusted under 35 U.S.C. 154(b) by 0 days.

(21) Appl. No.: 15/546,903

(22) PCT Filed: Jan. 25, 2016

(86) PCT No.: PCT/ES2016/070039
§ 371 (c)(1),
(2) Date: Jul. 27, 2017

(87) PCT Pub. No.: WO2016/124800
PCT Pub. Date: Aug. 11, 2016

(65) Prior Publication Data
US 2018/0031505 A1    Feb. 1, 2018

(30) Foreign Application Priority Data
Feb. 2, 2015    (ES) .................................. 201530127

(51) Int. Cl.
*G01R 27/28*    (2006.01)
*G01N 27/07*    (2006.01)
(Continued)

(52) U.S. Cl.
CPC .............. *G01N 27/07* (2013.01); *G01N 27/06* (2013.01); *G01N 33/2847* (2013.01); *G01R 27/22* (2013.01)

(58) Field of Classification Search
CPC ........ G01N 27/07; G01N 27/22; G01N 27/28; G01N 27/06; G01N 27/221;
(Continued)

(56) References Cited

U.S. PATENT DOCUMENTS

| 4,517,547 A | 5/1985 | Gray et al. |
| 5,343,156 A | 8/1994 | Johnson et al. |

(Continued)

FOREIGN PATENT DOCUMENTS

EP    0080755 B1    8/1986

OTHER PUBLICATIONS

International Search Report dated Mar. 7, 2016 for PCT/ES2016/070039 and English translation.

*Primary Examiner* — Thang X Le
(74) *Attorney, Agent, or Firm* — Lucas & Mercanti, LLP

(57) ABSTRACT

A method for measuring the presence of water in gas oil filters and a water sensor for carrying out is provided by a functional assembly associated with a pair of electrodes that are arranged in the area for decanting water which is separated from the fuel in the gas-oil filters, an electrical current being applied to said electrodes by a current source and a switching bridge, in measurement cycles separated by periods of electricity, each cycle being determined as a current pulse train, the polarization of the electrodes being adapted in the first measurement cycle in order to optimize the detection of water in the medium containing same, adjusting the functional activity acting on the duration of the current pulses when the presence of water is detected.

10 Claims, 3 Drawing Sheets

(51) Int. Cl.
*G01R 27/22* (2006.01)
*G01N 27/06* (2006.01)
*G01N 33/28* (2006.01)

(58) Field of Classification Search
CPC ........... G01N 33/2847; G01N 33/2888; G01N 33/26; G01N 21/8507; G01N 21/552
See application file for complete search history.

(56) References Cited

U.S. PATENT DOCUMENTS

| | | | |
|---|---|---|---|
| 5,463,321 A * | 10/1995 | Matlock | G01N 27/06 324/149 |
| 5,973,503 A | 10/1999 | Kuipers et al. | |
| 6,278,281 B1 * | 8/2001 | Bauer | G01N 27/221 324/441 |
| 6,278,282 B1 | 8/2001 | Marszalek | |
| 6,861,851 B2 * | 3/2005 | Lvovich | G01N 33/2888 324/553 |
| 8,007,655 B2 * | 8/2011 | Danyluk | G01N 33/2888 204/404 |
| 9,488,611 B2 * | 11/2016 | Rezvani | G01N 27/06 |
| 2004/0036487 A1 | 2/2004 | Heremans et al. | |
| 2008/0257867 A1 * | 10/2008 | Malshe | B81C 1/00492 219/69.14 |
| 2009/0216464 A1 | 8/2009 | Kong et al. | |
| 2009/0315571 A1 * | 12/2009 | Rajagopalan | G01N 27/06 324/691 |

* cited by examiner

US 10,274,445 B2

METHOD FOR MEASURING THE PRESENCE OF WATER IN GAS OIL FILTERS AND WATER SENSOR FOR CARRYING OUT SAID METHOD

CROSS REFERENCE TO RELATED APPLICATIONS

This Application is a 371 of PCT/ES2016/070039 filed on Jan. 25, 2016, which, in turn, claimed the priority of Spanish Patent Application No. P201530127 filed on Feb. 2, 2015, both applications are incorporated herein by reference.

TECHNICAL FIELD

The present invention is related to the detection of the accumulation of water in fuel filters of diesel engines, proposing a method for measuring the presence of water for that function and a sensor that allows said method to be carried out in advantageous conditions, using a conductivity system which reduces the harmful influences on electrodes which are in contact with the water-fuel medium to be controlled.

STATE OF THE ART

In the field of filtration and fuel injection systems for diesel engines, it has been known for a long time that there is a need to separate water, which, as a result of contamination in manufacturing and storing processes, or due to intentional adulteration, may be present in the fuel (gas oil), with the aim of preventing water from coming into contact with sensitive elements of the injection system of the engine to which it is applied, in which water may have a damaging effect due to the phenomenon of corrosion.

This function of separating water may be integrated into the fuel filter of the engine of the system of application in the case of small vehicles, or a special filter may be used, known as a water separator, in other applications. In any of the cases, the water that is separated from the fuel is decanted and stored in a specific suitable area, which, due to the fact that water is denser than gas oil, is usually located in the lower part of the housing of the filter or water-separating element.

Said function of separating and storing the water is often complemented by a sensor that detects the accumulation of water, which provides a signal when the accumulation of water has reached a predetermined maximum level in the decanting area, in order for the accumulated water to be purged or extracted, before causing damage.

There are basically two detection systems for the accumulation of decanted water in gas oil filters:

1) A float system and reed switch, consisting of a float provided with a magnet, the float being sized such that when it is submerged in a container that contains water and gas oil, it floats in the water which, due to the fact that it is denser, remains in the lower part, and it sinks in the gas oil which, in turn, floats on the water, and therefore, as the water is decanted in the lower part of the container, the float moves upwards with the water level. Arranged in coordination with the float is a reed switch, such that when a predetermined water level is reached, due to the placement of the magnet, a change of state is produced by means of the activation or deactivation of the reed switch, which may be applied to activate a warning signal when the water reaches the maximum predetermined level.

This system has the advantage in that no electrical part is in contact with the liquid medium, such that damaging phenomena of corrosion is not produced. However, the disadvantage is that it is very fragile, highly sensitive to vibrations and blows, and furthermore, for a vertical assembly from the lower part in the filter of application, the design has to be very specific, while for a lateral assembly, the necessary design is completely different, which makes the availability of several different designs necessary, complicating the possibilities for the application thereof.

2) A conductivity system, consisting of using the conductivity difference between the water and gas oil, since gas oil is a good electrical insulator in the temperature range of application, while water has a conductivity in said temperature range which may be measured relatively easily.

Arranged in this system are two electrodes in contact with the liquid medium, electrodes which are generally polarized by means of a voltage source and a resistive voltage divider, or by means of a current source, such that the resulting voltage between the electrodes powers an electronic comparator, calibrated in order to be able to distinguish the less conductive water from the gas oil which is expected to be found as a result of the separation and decanting in the filters of application.

Currently almost all designs of systems of this type use a polarization of electrodes in direct current, which leads to phenomena of corrosion due to oxidation in the anode and non-soluble salt deposits on the cathode, phenomena which do not damage the electric connectivity between electrodes and, therefore, do not damage the operation of the sensor either, while the electrodes are maintained submerged in water, but when the water is purged and eliminated, the electrodes enter into contact with the gas oil, the gas oil being absorbed by the crystalline structure of the deposits, forming an insulating layer which is not eliminated when the electrodes once again come into contact with the water, which degrades the sensor's capability with respect to the effectiveness of detecting subsequent water accumulations in the filter of application.

From the electrochemical theory, however, it is known that many of the reactions of oxidation that take place in the anode or positive electrode of the aforementioned sensors are reversible if in a short enough time the polarity of current between the electrodes is inverted. Furthermore, the precipitation reactions, such as the transformation of calcium bicarbonate into carbonate, which in a sensor with polarization of electrodes with direct current, prevail in the negative electrode or cathode, with a polarity inversion taking place alternatively in one electrode and the other, according to the polarity of the same at each moment, thereby increasing the time of the functional effectiveness of the sensor, since the each one of the electrodes receives half of the precipitations.

Therefore, polarizing the electrodes of the water sensors with alternating current, from a theoretical point of view, has advantages which potentially lengthen the life of said sensors in their application in gas oil filters, wherein they are subjected to successive cycles of contact with the water, which is decanted, and with gas oil. In practice, however, a significant benefit is not usually obtained in this sense, due to the fact that embodiments of sensors which use polarization of the electrodes with alternating current do not adequately use alternating current potential, since it does not take certain parameters and characteristics of the environment of application into consideration.

OBJECT OF THE INVENTION

In accordance with the invention, a measuring method is proposed for detecting the accumulation of decanted water in gas oil filters, using a detector which enables said method to be used in advantageous conditions.

The measuring method, object of the invention, uses a sensor provided with electrodes that are polarized, either with direct current or alternating current, by means of a control governing the connection, disconnection or alternation of the current.

According to said method of the invention, the sensor is not continuously polarizing the electrodes and measuring, but rather carrying out short measuring cycles (a few seconds), separated by periods of inactivity. And, if applicable, each measuring cycle is determined as a current pulse train, separated by very short disconnection periods.

During the first measuring cycle, an adaptation of the polarization conditions of the sensor's electrodes is carried out, with the aim of optimizing the analysis in detecting if water is present in the medium being measured, and if water is detected, adjusting the functional activity acting on the duration of the current pulses.

Therefore, initially a current at a specific level (for example 10 µA) is applied to the electrodes and the voltage obtained between the electrodes is checked, such that if said voltage is at a low level (for example around 1 volt), it means that the electrodes are in a high conductivity medium, justifying the presence of water; and if the voltage that is obtained has a considerably high value (such as around 3.5 volts), it means that the electrodes are in an insulated medium or a medium with a reduced conductivity, which may be gas oil or water with low conductivity.

In these conditions, when the voltage obtained between the electrodes is high (around 3.5 volts), to determine whether the medium is gas oil or water with low conductivity, the current applied is reduced to a significantly lower value (for example 1 µA) and the voltage obtained between the electrodes is once again checked, such that if the voltage value continues to be high, it confirms that the medium in which the electrodes are found is clearly gas oil, while if the voltage obtained in these conditions is of an intermediate value (for example around 2 volts) the medium is water with low conductivity.

When the presence of water is detected, both if it is high conductivity or low conductivity water, a signal is activated communicating the presence of water and, maintaining the current value that has been applied to the electrodes, the duration of the current pulses is adapted such that the voltage between the electrodes during each pulse is maintained in the transient state in which it is growing, within a specific range; by which the effects of corrosion and the formation of deposits on the electrodes are minimized.

Once the aforementioned adjustment is made, the system only evaluates voltage values between the electrodes at the end of each current pulse in order to repeatedly confirm the presence of water; and in the case that in a cycle the presence of water is not confirmed, the process is initiated again in order to establish a new adjustment.

The functional assembly of the sensor used to carry out this method for measuring the presence of water comprises an input stage, which integrates the components necessary for an electric power supply from an automotive installation; a current source which generates a stabilized current; a switching bridge, which may have a structure in order to function with direct current or alternating current; signal conditioning, which makes the necessary adaptations in order to supply the voltage signal of the electrodes to an analog/digital convertor or a comparator; a controller, which governs the operation of the equipment; an output stage, which adapts the signal provided by the equipment for the coupling thereof to a controller aboard a vehicle; and protection against harmful external influences.

In this way, a method is achieved that offers advantageous features for efficiently detecting the accumulation of water decanted in gas oil filters, with the following characteristics:

Polarization of the electrodes by means of a current source, allowing for a constant current between the electrodes, independent of the water resistivity, such that the value of the resistance between the electrodes may be directly obtained by simply measuring the voltage between the same, without the need for any other external parameter, such as voltage from the power supply, polarization resistance, etc. And furthermore, precise control of the level of the bias current allows the chemical reactions taking place in the electrodes (such as oxidation and precipitation deposits) to be under control, as well as the effects of the leakage resistance of the insulating materials in which the electrodes are embedded, or of electronic components.

The voltage between the electrodes is not treated by means of an analog transmission chain, but rather is digitalized at the beginning of the transmission chain to thereby allow for a subsequent numeric treatment of the signal.

The electrodes are not constantly polarized, but rather intermittently polarized, following a strategy that is compatible with obtaining information on the presence of water quickly enough in order to prevent a dangerous exceedance of a predetermined maximum level. This is achieved by means of the activation and deactivation of the current source, by means of a switch or assembly of solid state switches, controlled by a central unit integrated in the sensor. During the measuring cycle, there may be digital signal processing, with the aim of helping the analysis process and decision-making with regard to the presence or lack of presence of water.

The signal of the presence of water is transmitted to the outside once the detection process has finished and during the signaling phase on the outside, the electrodes are not polarized, reducing the phenomena of oxidation and precipitation, which provides an increase in the durability of the sensor, in addition to making it more immune to electromagnetic-type disturbances.

The signal of the presence of water is transmitted in an uninterrupted manner until the next power cycle, when the engine is disconnected, during which the sensor is disconnected from its power supply, being connected once again in the next power cycle, in order to return to the detection mode and carry out a new detection cycle after carrying out a self-test.

Advanced diagnostics are possible, such that the sensor may, for example, activate a specific output value if the signal between the electrodes corresponds to a signal of an old sensor, indicating that the sensor must be cleaned or substituted.

It is optionally possible to have a digital output protocol, which is able to transmit numeric values.

If a numeric type output protocol is implemented, the sensor may also be combined with others that are found in the same system, for example, pressure or temperature sensors, taking advantage of the characteristics of numeric protocols.

Furthermore, running on direct current, the frequency of the signal that is applied to the electrodes is variable, able to make a frequency sweep, in part of or in all the measuring cycles, with a low frequency (for example around 500 Hz), in order to precisely determine the nature of the liquid medium in which the electrodes of the sensor are located, and based on this fact, adapt the characteristics of the subsequent detection cycles, with the goal of maximizing the effectiveness of the sensor, and, at the same time minimizing the effects of the deposits and corrosion which result from the self-adapting system.

Therefore, the method, object of the invention, results from advantageous functional characteristics for the function of detecting water in gas oil filters, acquiring a life of its own and being preferred with respect to conventional systems which are used for the same function.

DETAILED DESCRIPTION OF THE INVENTION

The object of the invention relates to a method and a sensor for measuring the presence of water decanted in gas oil filters, particularly in diesel engines in vehicles, with the goal of emitting a warning signal when said accumulation of water reaches a maximum level established for purposes of safety, in order to prevent the water from causing damage to the system of application.

The method of the invention is based on measuring the electric conductivity between electrodes (5) which are arranged submerged in the medium which is to be controlled, applying a current signal in short cycles (a few seconds) to said electrodes (5), separated by periods of inactivity in which the current supply is disabled by means of a control system.

Figure 1:
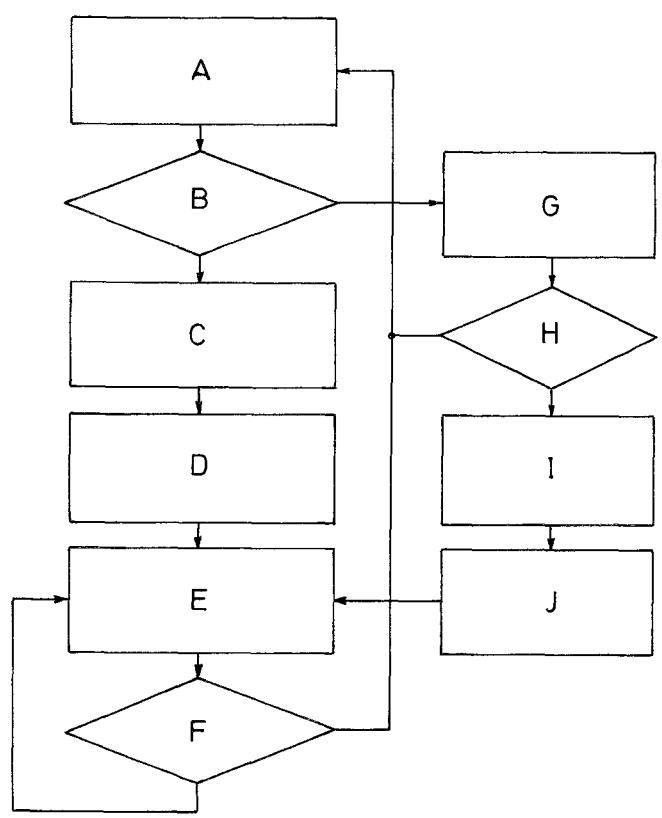
FIG. 1 shows a block diagram of the adaptation of the polarization which is applied to the electrodes of the method for measuring the presence of water according to the invention.

Each measuring cycle is made up of a current pulse train, separated by very short disconnection periods, adapting to the conditions of the polarization of the electrodes (5) in the first measuring cycle with the aim of optimizing the process of distinguishing whether or not there is water in the medium in which they are submerged, according to the process schematically represented in FIG. 1, which comprises the following phases:

A) A current $I_{max}$ (for example of 10 μA) made up of pulses of a predetermined maximum duration $t_{max}$ is injected into the electrodes (5).

B) The voltage transient obtained between the electrodes (5) is characterized, checking the voltage value reached and the stabilization time; determining if the final voltage is close to a low value $V_1$ (for example around 1 volt), which corresponds to a high conductivity medium, justifying the presence of water, or close to a value that is considered high $V_2$ (for example around 3.5 volts), which corresponds to an insulating medium or a medium with a reduced conductivity, which may be gas oil or water with low conductivity.

C) If the voltage has a low value $V_1$ which means that the medium in which the electrodes (5) are found is water, a signal is activated communicating the presence of water.

D) Maintaining the value of the current applied to the electrodes (5), the duration of the current pulses is adapted such that the voltage between the electrodes (5) during each pulse, in the transient state in which it is growing, does not exceed the limit between the transient state and the permanent state, regardless of the polarity. The optimal duration of each current pulse may vary between a maximum value $t_{max}$ and a minimum value $t_{min}$ for example, 5 milliseconds and 0.5 milliseconds, respectively.

E) The frequency of the application of the current pulses is adapted to the electrodes (5) based on the time of the duration of the pulses determined in the previous phase.

F) Once the adaptation of the polarization is done in the first measuring cycle, in the following measuring cycles, only the voltage value between the electrodes (5) is evaluated at the end of each current pulse in order to confirm the presence of water: such that if said presence is confirmed, the application of the frequency of the pulses is repeated, in order to successively confirm the presence of water and, if in a pulse the check does not reflect the presence of water, the adjustment process is initiated again starting with the first phase (A).

G) Alternatively, if in phase (B) the result of the voltage between the electrodes (5) is a high value $V_2$, which corresponds to an insulating or reduced conductivity medium, in order to determine if it is gas oil or water of low conductivity, the current which is applied is reduced to an essentially lower value $I_{min}$ (for example 1 μA).

H) The voltage that results between the electrodes (5) is checked again when applying that current $I_{min}$, such that if in these conditions the voltage returns to a high value $V_2$, it is confirmed that the medium in which the electrodes (5) are found is indeed gas oil, initiating the adjustment process again starting with phase (A).

I) If in checking when current $I_{min}$ is applied the voltage obtained has an intermediate value $V_3$ (for example around 2 volts), it means that the medium in which the electrodes (5) are located is water with low conductivity, in which case the signal for the presence of water is activated.

J) The pulses of the current $I_{min}$ are adapted to maintain the duration of the same between a $t_{max}$ time and a $t_{min}$ time, passing from phase (E) to continue the process according to that which was explained above.

The signal of the presence of water, obtained in any of the cases by means of the measuring process, is transmitted continuously in order to activate a warning indicator of the circumstance of the presence of water in the filter of application, keeping the signal active until the power of the engine in the corresponding vehicle is disconnected, once again carrying out an evaluation of the presence of water once the power of the engine is connected.

Figure 2:
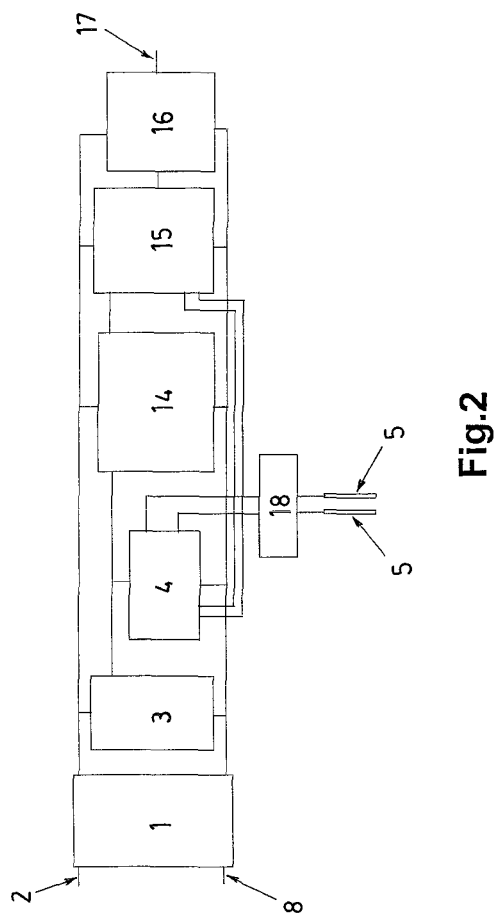
FIG. 2 shows a block diagram of the functional assembly of the sensor used for said method for measuring the presence of water according to the invention.

FIG. 2 schematically shows the functional assembly of the sensor used to carry out said method for measuring the presence of water in a gas oil filter according to the invention, said sensor comprising:

An input stage (1) in which there are the protection, limiting and filtering components necessary for electric power supply (2) from a typical automotive network.

A current source (3) which generates a stabilized current with a precision of around 1%. This current source (3) may be with the outgoing current, according to the embodiment represented in the diagram; however, it may also be, without altering the concept of the invention, according to a sink type embodiment, meaning with incoming current.

A switching bridge (4) which establishes a change of state in the connection of a pair of electrodes (5) which make up the part of the detector which is submerged in the liquid medium of application to detect the presence of water.

Figure 3:
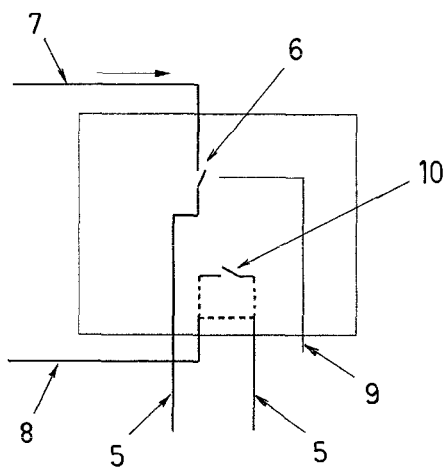
FIG. 3 is a diagram of the switching bridge of the sensor according to an embodiment in order to function with direct current.

This switching bridge (4) may have a configuration for the operation of the sensor with direct current, according to the example in FIG. 3, having a switch (6) between the electric connection (7) of one of the electrodes (5), while the other electrode (5) has a connection (8) to ground, such that with said switch (6), automatically actuated in the closing and opening by a control signal (9), the passage of the current coming from the current source (3) is activated and deactivated. This way, each electrode (5) always has the same configuration, the anode being that through which the current coming from the current source (3) enters, and the cathode being that which receives the current after passing through the medium in which the electrodes (5) are found.

In this configuration, it is further envisaged that the other switch (10) for disconnecting the electrode (5) that is connected to ground is included, with the goal of preventing, in the case of a difference in the ground potential of the filter of application and the ground potential of the sensor, a current from flowing between said electrode (5) connected to ground and the metal casing of the filter, causing a continual ageing of that electrode (5) connected to ground, even if the other electrode (5) is disconnected by the switch (6).

Figure 4:
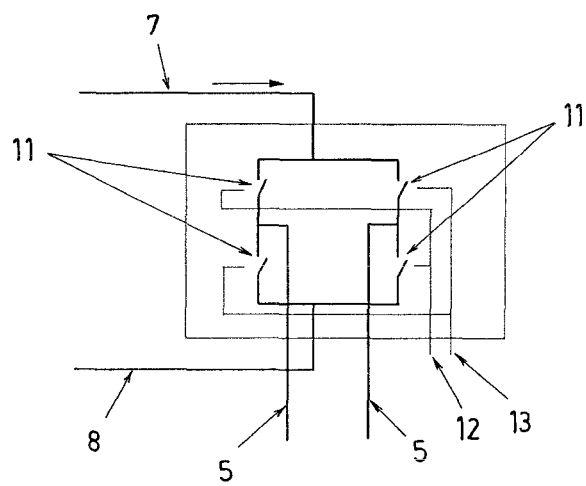
FIG. 4 is a diagram of the switching bridge of the sensor according to an embodiment in order to function with alternating current.

The switching bridge (4) may also have a configuration for the operation of the sensor with alternating current, according to the example in FIG. 4, having an H structure with four switches (11) which are automatically actuated in pairs by both control signals (12) and (13), being connected to the electrodes (5) of the sensor between said switches (11) of the aforementioned H structure. With this arrangement, because of the switches (11), the current that comes from the current source (3) may enter alternately, through one electrode (5) and then the other, which, depending on whether the current enters or exits through them, alternate in the function of the anode and the cathode. This configuration allows a variable frequency to be used, such that starting with a low frequency (for example around 500 Hz), analyzing the response of the electrodes (5) with different frequencies, it is possible to determine the minimum frequency for effectively detecting a passage of current between the same, which means that there is water in the medium in which they are submerged.

With alternating current, the same effect may be obtained by means of a structure of two generators of current with opposite signs (source and sink) and two switches, instead of the H structure with four switches (11) as shown in FIG. 4.

The functional assembly is complemented with a signal conditioner (14), which analyzes the changes in level, impedance adaptation and filtering, which are necessary to optimally supply the voltage signal of the electrodes (5) to an analog/digital converter. Optionally, instead of an analog/digital converter, a comparator may be used, in which the analog input signal is compared, to later be processed with a determined threshold, which may be variable, allowing a functionality of digitalization and analysis to be obtained, which is sufficient for some applications at a lower cost than through digitalization with an analog/digital converter.

The general control of the sensor is done by a controller (15) which is a microprocessor-type device, provided with an integrated analog/digital converter and the necessary input/output peripherals for the control connections of the functional components of the sensor and the numeric processing of the signal which is obtained from the electrodes (5) for the application thereof to an output stage (16), which is an analog block which in turn adapts the signal coming from the controller (15) such that there is a suitable coupling with the control system that will receive the signal (17) supplied by the sensor, particularly with the control system of a vehicle, in order to determine the presence of water in the fuel filter of the same.

In order to avoid harmful influences which may cause the sensor to malfunction, the functional assembly includes protections (18) against erroneous connections, short-circuiting, electromagnetic interference or electrostatic discharge, which are typical in automotive applications.

The invention claimed is:

1. A method performed by a sensor for measuring the presence of water in gas oil filters in order to detect the presence of water in a medium, the method comprising electrodes submerged in the medium, based on a voltage that results between said electrodes when applying an electric current to said electrodes, wherein in the electrodes an electric current is applied in measuring cycles separated by periods of inactivity, each measuring cycle determined as a current pulse train, the polarization of the electrodes being adapted in a first measurement cycle by means of the application of an electric current at a specific level to check if the voltage that results between the electrodes is a low value $V_1$ which corresponds to the presence of water in the medium in which the electrodes are submerged or a high value $V_2$ which corresponds to a medium in which the electrodes are found which is insulating or has a reduced conductivity, such that when the voltage exists between the electrodes, signaling the presence of water, a signal is activated alerting to the presence of water and maintaining the value of the electric current which has been applied to the electrodes, a duration of pulses of the applied electric current is adapted, such that the voltage between the electrodes in each current pulse is maintained in a transient state in which it is growing, within a specific range, later confirming the presence of water, repeatedly in each measuring cycle, evaluating the voltage value between the electrodes at the end of each current pulse.

2. The method for measuring the presence of water in gas oil filters, according to claim 1, wherein when the voltage obtained between the electrodes is of the high value $V_2$ which corresponds to an insulating or low conductivity medium, the current applied is reduced to a significantly lower value and the voltage obtained between the electrodes is once again checked in order to confirm if the high value $V_2$ remains high, reflecting that the medium in which the electrodes are found is gas oil, or if the voltage obtained is of an intermediate value $V_3$, reflecting that the medium in which the electrodes are found is water with low conductivity.

3. The method for measuring the presence of water in gas oil filters, according to claim 1, wherein when the voltage resulting between the electrodes reflects that the medium in which said electrodes are found is water, the duration of the current pulses which are applied are adapted between a maximum time of 5 milliseconds and a minimum time of 0.5 milliseconds.

4. A water sensor used in the measuring method of claim 1, comprising a functional assembly associated with a pair of electrodes for detecting the presence of water accumulated through decanting in a gas oil filter at a specific level, wherein the functional assembly comprises an input stage in which the connection of an electric power supply is established, a current source which generates a stabilized current, a switching bridge which establishes a change of state in the connection of the electrodes, a signal conditioner which supplies the voltage signal of the electrodes and an analog/digital convertor or a comparator, a controller which carries out a numeric processing of the signal received by the electrodes and an output stage which adapts the signal processed by the controller to be coupled to a receiver system of application.

5. The water sensor, according to claim 4, wherein the switching bridge has a configuration for operation with alternating current, having an H structure with four switches which are automatically actuated in pairs by control signals and, the electrodes being connected between said switches.

6. The water sensor, according to claim 4, wherein the switching bridge has a configuration for operation with direct current, having a structure of two generators of current with opposite signs (source and sink) and two switches.

7. The water sensor, according to claim 4, wherein the switching bridge has a configuration for operation with direct current, having a switch which is automatically actuated in closing and opening by a control signal, being placed between said switch in the electric connection of one of the electrodes, while the other electrode is connected to ground by means of a connection.

8. The water sensor, according to claim 7, wherein a cut-off switch is arranged in the connection to ground.

9. The water sensor, according to claim 4, wherein the functional assembly includes protection against external influences.

10. The water sensor, according to claim 4, wherein the controller is a microprocessor-type device.

* * * * *